United States Patent
Speldrich et al.

(10) Patent No.: US 12,386,370 B2
(45) Date of Patent: Aug. 12, 2025

(54) VOLUME FLOW RATE SMOOTHING DEVICE

(71) Applicant: Honeywell International Inc., Charlotte, NC (US)

(72) Inventors: Brian Speldrich, Freeport, IL (US); Jamie Speldrich, Freeport, IL (US); Ian Bentley, Manchester, NH (US)

(73) Assignee: Honeywell International Inc., Charlotte, NC (US)

( * ) Notice: Subject to any disclaimer, the term of this patent is extended or adjusted under 35 U.S.C. 154(b) by 188 days.

(21) Appl. No.: 18/316,540

(22) Filed: May 12, 2023

(65) Prior Publication Data
US 2024/0377846 A1    Nov. 14, 2024

(51) Int. Cl.
*G05D 7/01*    (2006.01)
*G01F 15/02*    (2006.01)

(52) U.S. Cl.
CPC ........... *G05D 7/0106* (2013.01); *G01F 15/02* (2013.01)

(58) Field of Classification Search
CPC .. G05D 7/0106; G01F 15/02; A61M 5/16886; A61M 2205/3341; A61M 2206/22; A61M 5/16877; F04B 11/0016; F16L 55/053
See application file for complete search history.

(56) References Cited

U.S. PATENT DOCUMENTS

| | | |
|---|---|---|
| 5,049,141 A | 9/1991 | Olive |
| 8,998,850 B2 | 4/2015 | Kamen et al. |
| 9,931,465 B2 | 4/2018 | Khalaj et al. |
| 2006/0149189 A1 | 7/2006 | Diamond et al. |
| 2008/0257410 A1* | 10/2008 | Walborn ........... A61M 5/16804 138/44 |
| 2011/0196303 A1* | 8/2011 | Chan .................. F04B 11/0008 604/151 |
| 2017/0361017 A1* | 12/2017 | Verma ............... A61M 5/16886 |

(Continued)

FOREIGN PATENT DOCUMENTS

EP    0258474 A1    3/1988

OTHER PUBLICATIONS

Satyendra, "Industrial Flow Measurements," IspatGuru, 23 pages, (Jun. 17, 2020). [Retrieved from the Internet Sep. 15, 2023: URL: <https://www.ispatguru.com/industrial-flow-measurements/>].

(Continued)

*Primary Examiner* — Francis C Gray
(74) *Attorney, Agent, or Firm* — Alston & Bird LLP (57) ABSTRACT

Various devices, assemblies, components, systems, and methods are provided relating to a volume flow rate smoothing device. An example smoothing device may include a body portion defining a chamber therein. The smoothing device may further include a first flow restrictor portion and a second flow restrictor portion each disposed in fluid communication with the body. The smoothing device may be configured to fluidically communicate with a pump via a first end of the smoothing device to receive a fluid flow from the pump along a fluid pathway extending through the first flow restrictor portion, the body portion, and the second flow restrictor portion. The first flow restrictor portion may be disposed upstream of the body portion. The second flow restrictor portion may be disposed downstream of the body portion.

19 Claims, 5 Drawing Sheets

(56) References Cited

U.S. PATENT DOCUMENTS

2020/0159112 A1    5/2020   Shackleton et al.
2020/0200313 A1    6/2020   Chu et al.
2021/0325916 A1*  10/2021   Lane ................... A61M 5/1452

OTHER PUBLICATIONS

Extended European Search Report Mailed on Oct. 4, 2024 for EP Application No. 24169728, 10 page(s).

* cited by examiner

VOLUME FLOW RATE SMOOTHING DEVICE

TECHNICAL FIELD

The present disclosure relates to a volume flow rate smoothing device capable of at least partially smoothing a pulsatile flow, which may facilitate improved delivery and/or improved measurement of the flow. Various systems and methods for smoothing a pulsatile flow and/or measuring a smoothed flow are also provided.

BACKGROUND

Some pumps can deliver unsteady flow (e.g., pulsatile flow) that may be difficult to accurately measure and may cause other downstream problems where flow rate is critical, such as medical applications. There is a need for devices and systems capable of accurate measurement of a pulsatile flow. Through applied effort, ingenuity, and innovation, Applicant has solved problems relating to volume flow rate smoothing devices by developing solutions embodied in the present disclosure, which are described in detail below.

BRIEF SUMMARY

Various embodiments of the present disclosure include smoothing devices, assemblies, smoothing assemblies, and corresponding systems, devices, components, and methods related to a volume flow rate smoothing device.

Various embodiments of the present disclosure may include a volume flow rate smoothing device. The smoothing device may include a body portion defining a chamber therein. The smoothing device may further include a first flow restrictor portion and a second flow restrictor portion each disposed in fluid communication with the body. The smoothing device may be configured to fluidically communicate with a pump via a first end of the smoothing device to receive a fluid flow from the pump along a fluid pathway extending through the first flow restrictor portion, the body portion, and the second flow restrictor portion. The first flow restrictor portion may be disposed upstream of the body portion. The second flow restrictor portion may be disposed downstream of the body portion.

In some embodiments, the first flow restrictor portion and the second flow restrictor portion may comprise the same minimum hydraulic diameter. In some embodiments, the volume flow rate smoothing device may further comprise a compliant component located within the body portion. In some embodiments, the compliant component may comprise a flexible membrane configured to contact the at least partially pulsatile fluid flow within the body portion. In some embodiments, the flexible membrane may be configured to separate the at least partially pulsatile fluid flow from at least a portion of air on an opposite side of the membrane. In some embodiments, the body portion may define a sealed air chamber comprising the at least a portion of air. In some embodiments, the body portion may be configured to permit external air to contact the membrane.

In some embodiments, the first flow restrictor portion may define a first hydraulic diameter. The first hydraulic diameter may be configured to be less than a hydraulic diameter of a tube configured to couple to the volume flow rate smoothing device at the first end of the volume flow rate smoothing device. In some embodiments, the second flow restrictor portion may define a second hydraulic diameter. The first hydraulic diameter may be configured to be less than the hydraulic diameter of the tube.

Various embodiments of the present disclosure may include a volume flow rate smoothing assembly. The volume flow rate smoothing assembly may include a volume flow rate smoothing device. The smoothing device may include a body portion defining a chamber therein. The smoothing device may further include a first flow restrictor portion and a second flow restrictor portion each disposed in fluid communication with the body. The smoothing device may be configured to fluidically communicate with a pump via a first end of the smoothing device to receive a fluid flow from the pump along a fluid pathway extending through the first flow restrictor portion, the body portion, and the second flow restrictor portion. The first flow restrictor portion may be disposed upstream of the body portion. The second flow restrictor portion may be disposed downstream of the body portion. The volume flow rate smoothing assembly may further include a first flow tube configured to operably connect to the first end of the volume flow rate smoothing device downstream of the pump. The volume flow rate smoothing assembly may further include a second flow tube configured to operably connect to a second end of the volume flow rate smoothing device downstream of the second flow restrictor portion.

In some embodiments, the volume flow rate smoothing assembly may further include at least one flow sensor. The at least one flow sensor may be disposed downstream from the at least one chamber along the fluid pathway. The at least one flow sensor may be configured to measure one or more properties of the fluid flow exiting the volume flow rate smoothing device. In some embodiments, the volume flow rate smoothing device may further comprise a compliant component located within the body portion. In some embodiments, the compliant component may comprise a flexible membrane configured to contact the at least partially pulsatile fluid flow within the body portion. In some embodiments, the flexible membrane may be configured to separate the at least partially pulsatile fluid flow from at least a portion of air on an opposite side of the membrane. In some embodiments, the body portion may define a sealed air chamber comprising the at least a portion of air. In some embodiments, the body portion may be open, such that the body may be configured to permit external air to contact the membrane.

In some embodiments, the assembly further may comprise a sensor disposed after the second flow restrictor portion. The sensor may be configured to receive the fluid after the fluid exits the second flow restrictor portion. In some embodiments, the fluid flow from the pump may be at least partially pulsatile.

Various embodiments may include a method for dispensing a fluid. The method may include a volume flow rate smoothing assembly. The volume flow rate smoothing assembly may include a volume flow rate smoothing device. The smoothing device may include a body portion defining a chamber therein. The smoothing device may further include a first flow restrictor portion and a second flow restrictor portion each disposed in fluid communication with the body. The smoothing device may be configured to fluidically communicate with a pump via a first end of the smoothing device to receive a fluid flow from the pump along a fluid pathway extending through the first flow restrictor portion, the body portion, and the second flow restrictor portion. The first flow restrictor portion may be disposed upstream of the body portion. The second flow restrictor portion may be disposed downstream of the body portion. The volume flow rate smoothing assembly may further include a first flow tube configured to operably connect to the first end of the volume flow rate smoothing device downstream of the pump. The volume flow rate smoothing assembly may further include a second flow tube configured to operably connect to a second end of the volume flow rate smoothing device downstream of the second flow restrictor portion. The method may further include pumping a fluid through the volume flow rate smoothing assembly along the fluid pathway with a pump. The pump may generate an at least partially pulsatile flow of the fluid. The volume flow rate smoothing device may at least partially smoothes the pulsatile flow.

The above summary is provided merely for purposes of summarizing some example embodiments to provide a basic understanding of some aspects of the present disclosure. Accordingly, it will be appreciated that the above-described embodiments are merely examples and should not be construed to narrow the scope or spirit of the present disclosure in any way. It will be appreciated that the scope of the present disclosure encompasses may potential embodiments in addition to those here summarized, some of which will be further described below. Other features, aspects, and advantages of the subject matter will become apparent from the description, the drawings, and the claims.

BRIEF DESCRIPTION OF THE FIGURES

The following drawings are illustrations of a particular embodiment of the present disclosure and therefore do no limit the scope of the present disclosure. The drawings are not necessarily drawn to scale and are intended for use in conjunction with the explanation in the following detailed description.

DETAILED DESCRIPTION

Some embodiments will now be described more fully hereinafter with reference to the accompanying drawings, in which some, but not all, embodiments are shown. Indeed, various embodiments may be embodied in many different forms and should not be construed as limited to the embodiments set forth herein; rather, these embodiments are provided so that this disclosure will satisfy applicable legal requirements. Like reference numerals refer to like elements throughout.

As used herein, terms of direction such as "front," "rear," "top," etc. are used for explanatory purposes in the examples provided below to describe the relative positions of certain components or portions of components to other components or portions of components described in the particular context indicated and should not be interpreted to require an absolute position relative to other points of reference (e.g., relative to the Earth). As used herein, the term "or" is used in both the alternative and conjunctive sense, unless otherwise indicated. The term "along," and similarly utilized terms, means near or on, but not necessarily requiring direct contact with a surface or other referenced location. The terms "approximately," "generally," and "substantially" refer to within manufacturing and/or engineering design tolerances for the corresponding materials and/or elements unless otherwise indicated. The use of such terms is inclusive of and is intended to allow independent claiming of specific values listed. Thus, use of any such aforementioned terms, or similarly interchangeable terms, should not be taken to limit the spirit and scope of embodiments of the present disclosure.

As used in the specification and the appended claims, the singular form of "a," "an," and "the" include plural references unless otherwise stated. The terms "includes" and/or "including," when used in the specification, specify the presence of stated feature, elements, and/or components; it does not preclude the presence or addition of one or more other features, steps, operations, elements, components, and/or groups thereof.

The phrases "in one embodiment," "according to one embodiment," "in some embodiments," "in various embodiments", and the like generally refer to the fact that the particular feature, structure, or characteristic following the phrase may be included in at least one embodiment of the present disclosure, but not necessarily all embodiments of the present disclosure. Thus, the particular feature, structure, or characteristic may be included in more than one embodiment of the present disclosure such that these phrases do not necessarily refer to the same embodiment.

As used herein, the terms "example," "exemplary," and the like are used to mean "serving as an example, instance, or illustration." Any implementation, aspect, or design described herein as "example" or "exemplary" is not necessarily to be construed as preferred or advantageous over other implementations, aspects, or designs. Rather, use of the terms "example," "exemplary," and the like are intended to present concepts in a concrete fashion.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

In various examples, a pump may produce a variable fluid flow rate over time (e.g., a pulsatile flow of liquid). The changes in the variable fluid flow rate over time (e.g., dQ/dt) may be greater than the sensitivity that a sensor can measure, which may lead to erroneous sensor readings. This may be caused, for example, by the particular mechanical and/or electrical characteristics of the pump (e.g., a peristaltic pump). Liquid sensors may be ill equipped to accurately measure the flow rate of a pulsatile fluid flow (e.g., a pulsing liquid flow), such that the sensor measurements may be inaccurate and/or erratic.

As described herein, the present disclosure includes various embodiments of a volume flow rate smoothing device configured to reduce the pulsatile fluid flow of a liquid exiting a pump. The volume flow rate smoothing device (also referred to as a "smoothing device") may be configured to at least partially dampen a pulsatile flow to produce a smoother flow of fluid into a downstream sensor. In some embodiments, the smoothing device may operate similar to low-pass filter for fluids. The smoothing device may include restrictions upstream and downstream of a chamber, which in combination, may serve to smooth the pulsatile liquid flow to produce a steadier flow for measurement by a liquid sensor.

In some embodiments, the depicted volume flow rate smoothing device may include a body portion, a first flow restrictor portion disposed on a first side (e.g., an upstream side), and a second flow restrictor portion disposed on a second side (e.g., a downstream side). In some embodiments, the body portion may define a chamber therein. In some embodiments, the first flow restrictor portion and the second flow restrictor portion are disposed in fluid communication with the body portion. In some embodiments, the volume flow rate smoothing device may receive a fluid flow from a pump along a fluid pathway, wherein the fluid pathway is configured to extend through the first flow restrictor portion, the body portion, and the second flow restrictor portion. During operation of a pump, the first flow restrictor portion, the second flow restrictor portion, and/or the body portion may serve to dampen or otherwise smooth an at least partially pulsatile flow from the pump.

In various embodiments the first flow restrictor portion and the second flow restrictor portion may be configured to have the same minimum cross-sectional area. The minimum cross-sectional area may be smaller than a respective flow tube that connects to each flow restrictor portion. In some embodiments, the minimum cross-sectional area may assist in smoothing the pulsatile fluid flow. In various embodiments, the body portion may further include a flow absorption component that may comprise a flexible membrane. The flexible membrane may contact at least partially the pulsatile fluid flow within the body. The flexible membrane may be further configured to assist with reducing the pulsatile fluid flow by expanding within the chamber.

Figure 1:
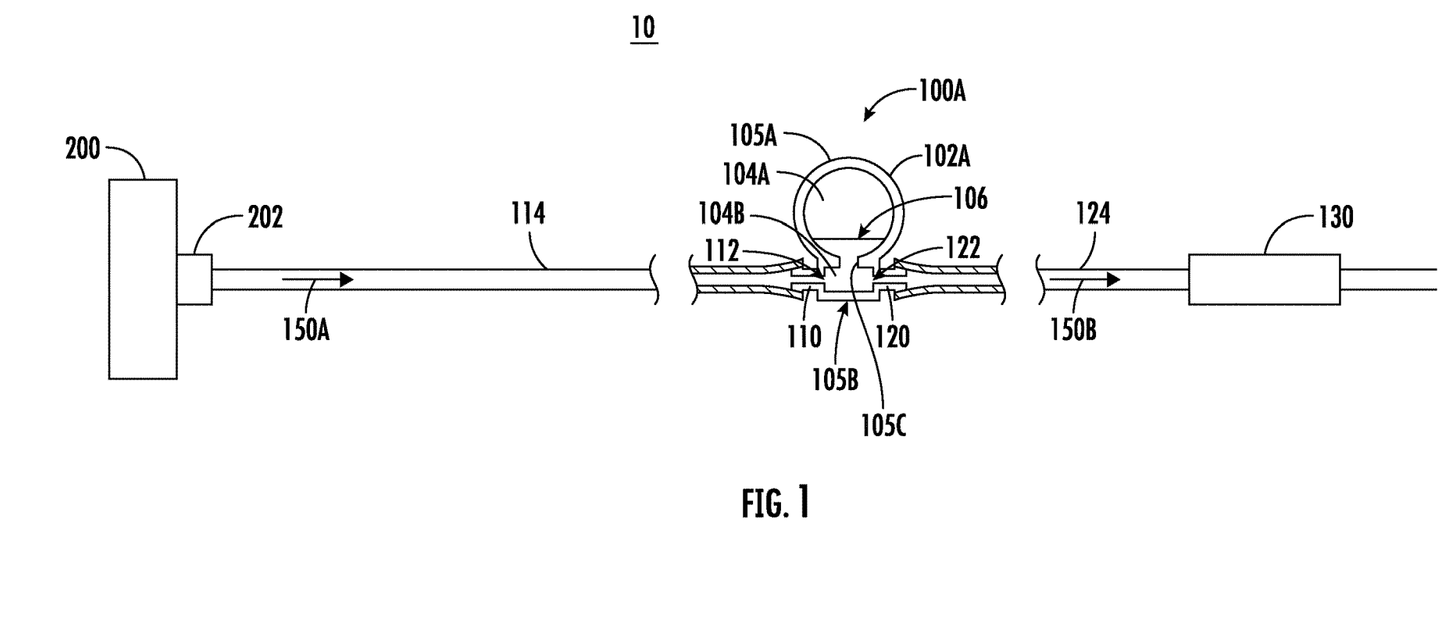
FIG. 1 illustrates a partial side view of an example volume flow rate smoothing assembly with a cross-sectional view of a volume flow rate smoothing device in accordance with various embodiments of the present disclosure.

FIGS. 1-6 depict views of example volume flow rate smoothing assemblies 10 and portions thereof in accordance with various embodiments of the present disclosure. FIG. 1 depicts a side cross-sectional view of a volume flow rate smoothing assembly 10, which in the depicted embodiment includes a volume flow rate smoothing device 100A, a pump 200, and at least one flow sensor 130. The at least one flow sensor 130 may include, by way of non-limiting example, positive displacement flow sensor, mass flow sensor, velocity flow sensor, volumetric flow sensor, thermally based sensor (e.g., MEMS, hotwire flow sensor, and/or the like), ultrasonic flow sensor, pressure sensor (e.g., a sensor capable of detecting a differential pressure across a drop, such as MEMS; an absolute pressure sensor, a gauge pressure sensor, and/or the like), etc. The volume flow rate smoothing assembly 10 may further include a first flow tube 114 and/or a second flow tube 124. In the depicted embodiment, the first flow tube 114 connects the pump 200 with the smoothing device 100A, and the second flow tube 124 connects the smoothing device 100A with the sensor 130, with the sensor 130 being positioned downstream of both the pump 200 and the smoothing device 100A. The first flow tube 114 and/or the second flow tube 124 may attach to the smoothing device 100A using, by way of non-limiting example, threaded fittings, Luer fittings, hose clamps, welded connections, adhesive, etc. In some embodiments, the sensor 130 and the smoothing device 100A may be part of the same physical structure, such as integrated into a common housing or rigidly attached to each other without a flexible flow tube therebetween. For example, the sensor 130 may be attached directly to the smoothing device 100A (e.g., just downstream of the second flow restrictor portion 120) or may be molded or otherwise formed as a single part or a part having a single housing with the smoothing device 100A. It will be appreciated that some embodiments may include individual components of the assembly 10 or portions thereof and/or sub-combinations of any of the devices described herein.

In some embodiments, the volume flow rate smoothing device 100A may include first flow restrictor portion 110, a second flow restrictor portion 120, and a body portion 102A. In the depicted embodiment, the body portion 102A, the first flow restrictor portion 110, and the second flow restrictor portion 120 form a single unitary component. With continued reference to FIG. 1, the body portion 102A may define at least one chamber(s) 104B. The chamber 104B may include a chamber inlet 112 disposed on a first side (e.g., upstream) of the body portion 102A and a chamber outlet 122 disposed on a second side (e.g., downstream) of the body portion. In some embodiments, the volume flow rate smoothing device 100A may be formed of a rigid material (e.g., rigid plastic).

Figure 4:
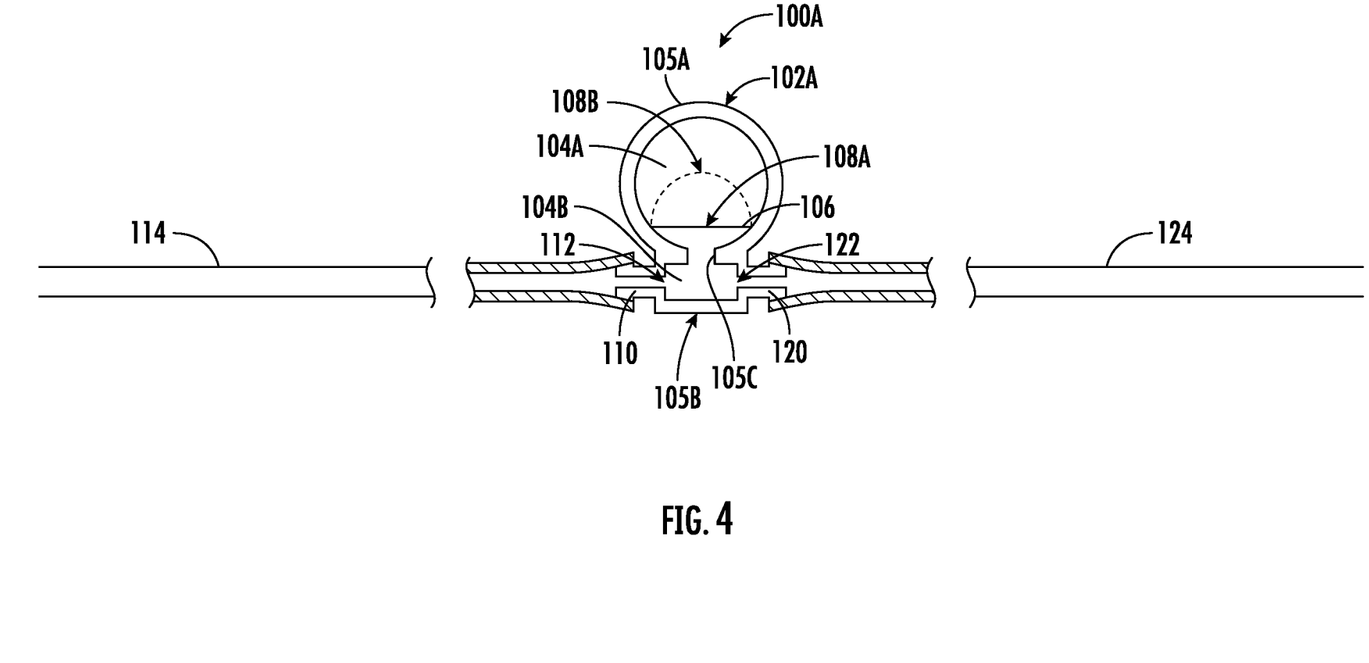
FIG. 4 illustrates a side cross-sectional view of an example volume flow rate smoothing device in accordance with various embodiments of the present disclosure.
Figure 5:
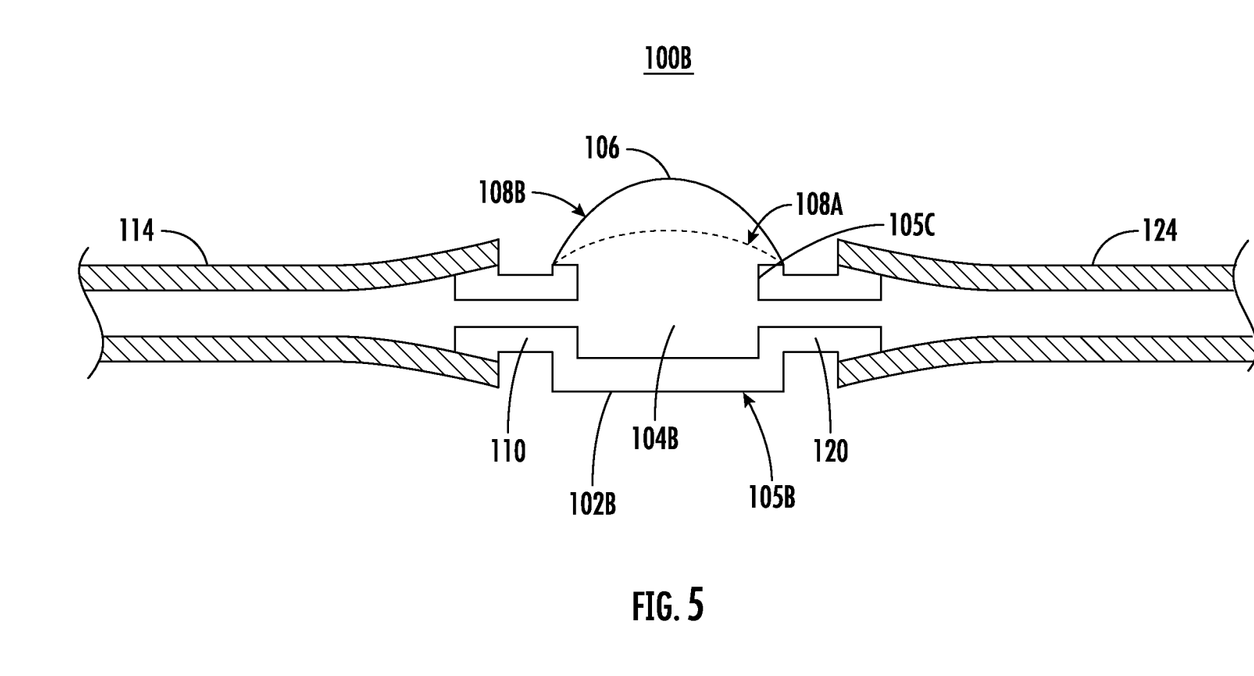
FIG. 5 illustrates a side cross-sectional view of an example volume flow rate smoothing device in accordance with various embodiments of the present disclosure.
Figure 6:
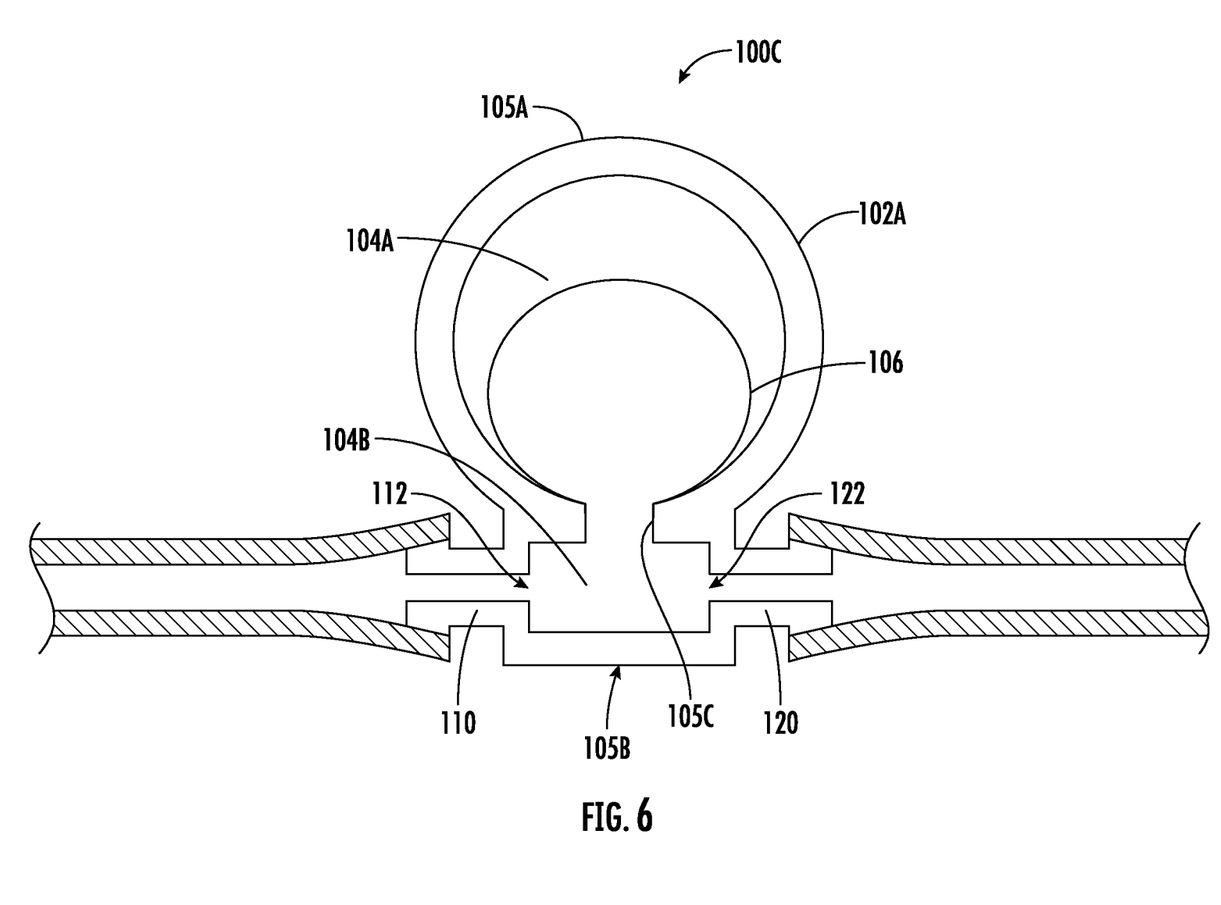
FIG. 6 illustrates a side cross-sectional view of an example volume flow rate smoothing device in accordance with various embodiments of the present disclosure.

In various embodiments, the volume flow rate smoothing device 100A includes a compliant component 106 disposed within the body portion 102A. The compliant component 106 may be flexible and may be configured to separate the chamber 104B from one or more of an external environment and a second chamber 104A. In some embodiments, the compliant component comprises a flexible membrane material (e.g., PVC sheet, latex, nylon, silicone, etc.) that may contact the at least partially pulsatile fluid flow within the body portion 102A. In some embodiments, the flexible membrane material may be a biocompatible material. In operation, the pulsatile flow operates to expand and stretch the compliant component 106. The compliant component 106 may at least partially absorb and reduce the energy of pulses in the flow through the smoothing device 100A. In the depicted embodiments, an outer perimeter of the compliant component 106 may attach to a portion of the body portion 102A (e.g., a circular segment of the inner wall as shown in FIGS. 1, 4, and 6, to the uppermost surfaces of the body portion 102B as shown in FIG. 5). The compliant component 106 may be attached to a portion of the body portion via any means including, by way of non-limiting example, glue, clamping, pinching beneath a top cap, etc. Thus, the compliant component 106 may remain stationary relative to the body portion 102A, 102B while a middle of the compliant component expands and contracts during flow of fluid through the smoothing device 100A, 100B, 100C.

In various embodiments, the compliant component 106 may further separate the chamber within the body portion 102A into at least two separate portions. In various embodiments (e.g., as shown in the embodiments of FIGS. 1, 4), the body portion 102A may be enclosed, such that the chamber 104B receives the at least partially pulsatile fluid flow, and a second chamber 104A includes a sealed, predetermined mass of air. The compliant component 106 may divide the chamber 104B and the second chamber 104A, such that the sealed, predetermined mass of air is on an opposite side of the compliant component 106 relative to the chamber 104B containing the pulsatile flow. In some embodiments (e.g., as shown in FIG. 5), the body portion 102B may define an open top (or another opening to an external environment) such that one side of the compliant component 106 defines the chamber 104B while the other side of the compliant component 106 is exposed to an external environment or otherwise in contact with a large and/or variable mass of air. The chamber 104B defined by the compliant component 106 may be a liquid receiving chamber portion, wherein the chamber 104B is fluidically communicative with the flow restrictor portions 110, 120. In various embodiments, the chamber 104B receives at least partial pulsatile fluid flow from the first flow restrictor portion 110. While the second chamber 104A is described as containing air in certain embodiments, the air may be replaced with any gas (e.g., nitrogen) or other compressible media.

In some embodiments, the body portion 102A may comprise two or more discrete shapes, including a bulbous expansion body 105A and a flow body 105B (shown in FIGS. 1, 4, 6). In the depicted embodiment of FIGS. 1, 4, 6, the bulbous expansion body 105A is an at least partially spherical shape and the flow body 105B is a cylindrical prism shape, with the bulbous expansion body and the flow body connected via an opening 105C. The chamber 104B may be defined at least by the flow body 105B and, in the embodiment shown in FIGS. 1, 4, 6, also partly by the bulbous expansion body 105A. In the embodiment shown in FIG. 5, the body portion 102B lacks a bulbous expansion body 105A and the compliant component 106 extends across the opening 105C. In various embodiments, the body portion 102A may comprise any shape (e.g., cylindrical, rectangular prism, hemispherical, etc.) and may be configured to perform the various functions described herein.

In various embodiments, the flexible membrane material of the compliant component 106, when contacting the at least partially pulsatile fluid flow of a fluid, may flex upwards (relative to the reference frame of the figures) at least absorbing and smoothing the pulses of the flow. The compliant component 106, when expanded upwards, shrinks the second chamber 104A and compresses the air therein at least partially in an instance in which the second chamber is sealed, such that both the air within the second chamber 104A and the compliant component 106 resist the forces of the fluid flow to at least partially create the smoothing effect. The compression of the sealed air may at least partially act like a shock absorber absorbing the pulsatile fluid flow, such that the fluid exiting the body portion 102A into the second flow restrictor portion 120 may be at least partially smoothed into a smoother flow.

In the depicted embodiments, the pump 200 is fluidically communicative with the volume flow rate smoothing device 100A and the flow sensor 130 via a fluid pathway that may be defined at least partially by the first flow tube 114, the first flow restrictor portion 110, the chamber 104B, the second flow restrictor portion 120, and/or the second flow tube 124. In various embodiments, the first flow tube 114 is configured to secure to a pump outlet 202 of the pump 200, or another connector comprising the pulsatile fluid flow from the pump, at a first end, and the first flow tube 114 is configured to secure to the first flow restrictor portion 110 at a second end. The second flow tube 124 may be configured to secure to the second flow restrictor portion 120 at a first end and the flow sensor 130 or another connector connecting to the flow sensor at a second end.

In the depicted embodiment of FIG. 1, the pump 200 and the first flow restrictor portion 110 are disposed upstream 140 of the body portion 102A, and the second flow restrictor portion 120 and the at least one flow sensor 130 are disposed downstream 150 of the body portion 102A. In various embodiments, the pump 200 may pump fluid from a storage container (not depicted) or other fluid supply out a pump outlet 202 to the fluid pathway defined in part by the first flow tube 114. The fluid may exit the pump outlet 202 with a predetermined average flow rate while the flow is also at least partially pulsatile. In various embodiments, the pulsatile fluid flow of a fluid from the pump may result in inaccurate measurement taken by at least one flow sensor 130 downstream from the pump. Further, the pulsatile fluid flow of the fluid may cause one or more alarms to be triggered due to the pulsing of the fluid, which may result in shutting off the pump automatically. The pump may be any pump known to create an at least partially pulsatile flow, such as a peristaltic pump, a syringe pump, a diaphragm pump, etc.

Figure 2:
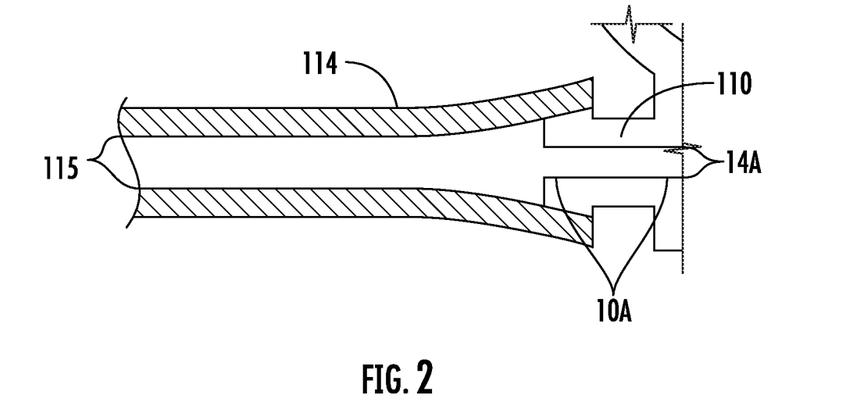
FIG. 2 illustrates a side cross-sectional view of an example first flow restrictor portion in accordance with various embodiments of the present disclosure.
Figure 3:
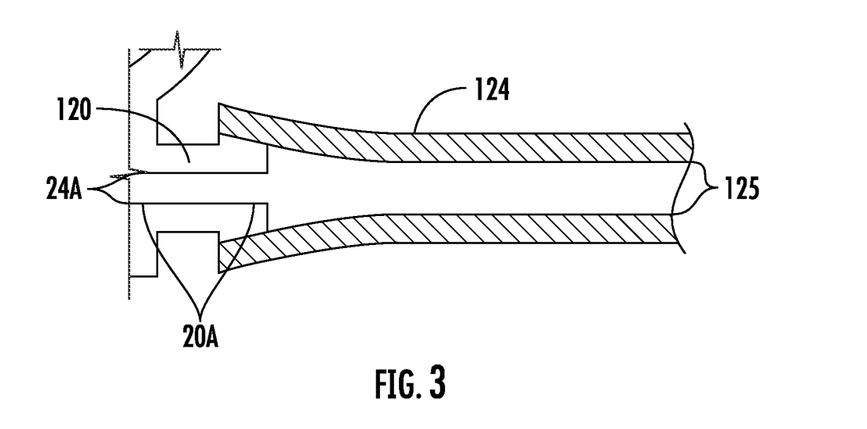
FIG. 3 illustrates a side cross-sectional view of an example second flow restrictor portion in accordance with various embodiments of the present disclosure.

The volume flow rate smoothing device may further comprise a first flow restrictor portion 110 and/or a second flow restrictor portion 120 to provide further smoothing of the pulsatile fluid flow. With reference to FIGS. 2-3, side cross-sectional views of an example first flow restrictor portion 110 and an example second flow restrictor portion 120 are depicted in accordance with various embodiments of the present disclosure. In the depicted embodiments in FIGS. 2-3, the first flow tube 114 secures to the first flow restrictor portion 110 and the second flow tube 124 secures to the second flow restrictor portion 120. The first flow tube 114 and the second flow tube 124 may secure to the respective flow restrictor portions 110, 120 by sliding over the flow restrictor portion. The tubes may be held thereon by ribs on the flow restrictor portions 110, 120, pipe clamps, hose clamps, threaded fittings, Luer fittings, or other securing structure and/or processes. The first flow tube 114 and the second flow tube 124 may comprise a flexible plastic material, such as soften polyvinyl chloride (PVC), polyethylene, polypropylene, etc.

In the depicted embodiments, the first flow restrictor portion 110 is upstream of the chamber 104B and the second flow restrictor portion 120 is downstream of the chamber 104A, such that smoothing is applied to the fluid flow prior to and following introduction of the fluid flow into the chamber 104B. While depicted as being integral the body portion 102A and formed of a single piece of material as the body portion, one or both the flow restrictor portions 110, 120 may be separately formed and attached (either permanently, such as by welding or adhesive, or temporarily, such as via a tube and/or clamp) to the body portion.

The first flow restrictor portion 110 defines a first flow restrictor cross-sectional area 14A (e.g., measured perpendicular to the direction of flow) and a first length 10A, and the second flow restrictor portion 120 defines a second flow restrictor cross-sectional area 24A and a second length 20A. In some embodiments, the cross-sectional area may remain constant along the length of the flow restrictor portions 110, 120 or may vary along the length of the flow restrictor portions. In some embodiments, the "cross-sectional area" may refer to an average area over the length of the restrictor portion(s), may refer to a minimum area for the restrictor portion(s), and/or may refer to an instantaneous area at one or more longitudinal locations along the length of the restrictor portion(s). In some embodiments, the first flow restrictor cross-sectional area 14A is equal to the second flow restrictor cross-sectional area 24A. In some embodiments, the first flow restrictor length 10A is equal to the second flow restrictor length 20A.

The first flow restrictor cross-sectional area 14A and the second flow restrictor cross-sectional area 24A may be defined as a minimum cross-sectional area of the restrictors when taken along their respective lengths. The minimum cross-sectional area or other property(ies) of the restrictors may be predetermined based on the desired application, the desired fluid flow, the desired flow velocity, the desired flow pressure, the flow tube shapes, etc. The cross-sectional shapes of the flow restrictor portions 110, 120 may be circular (e.g., the flow restrictor portions 110, 120 may be round tubes). In some embodiments, the cross-sectional shape of the first flow restrictor portion 110 and/or the second flow restrictor portion 120 may be at least partially non-circular. In some embodiments, the cross-sectional shape of the first flow restrictor portion 110 and/or the second flow restrictor portion 120 may vary at least somewhat along their lengths. In an example embodiment, the length of the first flow restrictor portion and the second flow restrictor portion may equal 10.16 mm and the radius may equal 0.508 mm. In some embodiments, the length 10A of the first flow restrictor portion 110 and/or the length 20A of the second flow restrictor portion 120 may be within 5% of 10.16 mm (e.g., greater than or equal to 9.652 mm and less than or equal to 10.668 mm) or within 10% of 10.16 mm (e.g., greater than or equal to 9.144 mm and less than or equal to 11.176 mm). In some embodiments, the radius of the first flow restrictor portion 110 and/or the radius of the second flow restrictor portion 120 may be within 5% of 0.508 mm (e.g., greater than or equal to 0.4826 mm and less than or equal to 0.5334 mm) or within 10% of 0.508 mm (e.g., greater than or equal to 0.4572 mm and less than or equal to 0.5588 mm). In some embodiments, the first flow restrictor cross-sectional area 14A may be equal to the second flow restrictor cross-sectional area 24A. The cross-sectional area of the first flow restrictor portion 110 and/or the second flow restrictor portion 120 may similarly be within a predetermined range (e.g., within 5% or 10% of the calculated cross-sectional area, or within the range resulting from the radii discussed above). In some embodiments, the first flow restrictor minimum cross-sectional area 14A may be equal to the second flow restrictor minimum cross-sectional area 20A. In some embodiments, the bulbous expansion body 105A may define a predefined volume. For example, in some embodiments, the bulbous expansion body 105A may have a radius of 13.5 mm. In some embodiments, the radius of the bulbous expansion body 105 may be within 5% (e.g., greater than or equal to 12.825 mm and less than or equal to 14.175 mm) or 10% (e.g., greater than or equal to 12.15 mm and less than or equal to 14.85 mm). The flow restrictor portions 110, 120 in combination with the body portion 102A may effectively provide hydraulic low pass filtering and may smooth the at least partially pulsatile fluid flow of the fluid, such that the fluid flow leaving the volume flow rate smoothing device 100A is smoother than it arrived. In some embodiments, the shape of the flow restrictor portions 110, 120 may be similarly represented as the hydraulic diameter of the restrictor portions, which may be determined regardless of the shape of the restrictor portion. The hydraulic diameter may represent a hypothetical diameter of a rounded tube having at least partially equivalent properties to the actual shape of the flow restrictor portions. In some embodiments, hydraulic diameter may be expressed as $D_H=(4A)/P$ where A is the cross-sectional area of the flow restrictor portion and P is the internal wetted perimeter. The hydraulic diameter may be used based upon any of the aforementioned measurements assuming a round tube for the dimensions given above. The hydraulic diameter may be measured at one or more particular flow-directional locations with the restrictors and/or may be an average or minimum value measured over a predetermined length (e.g., a full length of the flow restrictor or a portion thereof).

In various embodiments, the first flow tube 114 comprises a first flow tube cross-sectional area 115, wherein the first flow tube cross-sectional area 115 is greater than that of the first flow restrictor cross-sectional area 14A. The second flow tube 124 comprises a second flow tube cross-sectional area 125, wherein the second flow tube cross-sectional area 125 is greater than that of the second flow restrictor cross-sectional area 24A. The larger cross-sectional areas of the first flow tube 114 and the second flow tube 124 may allow for the flow tubes to at least partially surround the ends of the respective flow restrictor portions 110, 120 connecting the flow tubes to the flow restrictor portions (e.g., via a barbed outer perimeter of the flow restrictor portions, via a hose clamp, or similar attachment). The connecting of the flow tube with the flow restrictor portions allows for the first flow tube 114 and the second flow tube 124 to fluidically communicate with each other via the chamber 104B disposed between the two flow restrictor portions 110, 120. In various embodiments, the pulsatile fluid flow of the fluid flows from the pump along the portion of the fluid pathway defined by the first flow tube 114 towards the first flow restrictor portion 110. The first flow restrictor 110 causes the pulsatile fluid flow to initially reduce the pulsing of the fluid flow before entering the chamber 104B of the r body portion 102A, the body portion 102A further reduces the pulsing of the fluid further, and the second flow restrictor portion 120 controls flow within the body portion 102A and further restricts and reduces the pulsing of the fluid flow. The average fluid flow rate from the pump 200 is the same as the average fluid flow rate into the sensor 130, while the instantaneous fluid flow rate at the sensor for any given time is expected to be closer to the average than the instantaneous fluid flow rate leaving the pump, which can vary due to the pulsatility of the fluid leaving the pump.

With further reference to FIGS. 2-3, in various embodiments, the first flow restrictor portion 110 and the second flow restrictor portion 120 may comprise identical shapes that are reversed relative to the flow direction. Both flow restrictor portions define respective portions of the fluid pathway through the assembly 10. The first flow restrictor portion 110 may define the chamber inlet 112 into the chamber 104B and the second flow restrictor portion 120 may define the chamber outlet 122 from the chamber 104B.

FIG. 4 illustrates a first embodiment of the volume flow rate smoothing device 100A comprising a body portion 102A, a first flow restrictor portion 110, and/or a second flow restrictor portion 120. The compliant component 106 comprises a flexible membrane material that is illustrated flexing from a first position 108A to a second position 108B under pressure of the fluid flow (e.g., at $Q_{max}$, the compliant component 106 may be in the second position 108B while at $Q_{min}$ and/or no-flow, the compliant component 106 may be in the first position 108A). In the depicted embodiment of FIG. 4, the compliant component 106 outer perimeter secures to an inner wall of the bulbous expansion body 105A.

FIG. 5 illustrates a second embodiment of the volume flow rate smoothing device 100B comprising a second body portion 102B with no sealed air volume for resisting the flexing of the compliant component 106. The compliant component 106 comprises a flexible membrane material that is illustrated flexing from a first position 108A to a second position 108B under pressure of the fluid flow (e.g., at $Q_{max}$, the compliant component 106 may be in the second position 108B while at $Q_{min}$ and/or no-flow, the compliant component 106 may be in the first position 108A). In the depicted embodiment of FIG. 5, the compliant component 106 outer perimeter secures to an upper wall of the flow body 105B and the body portion 102B lacks a bulbous expansion body. Apart from the operation of the compliant component 106 and the absence of a bulbous expansion body, the body portion 102B and smoothing device 100B may be structured and may operate in the same manner as the respective body portion 102A and volume flow rate smoothing device 100A described with respect to FIGS. 1-4. The second body portion 102B may be readily substituted into any embodiment described herein.

With continued reference to the embodiment of FIG. 5, the pulsatile fluid flow enters the volume flow rate smoothing device 100B via the first flow restrictor portion 110, wherein the depicted first flow restrictor portion may comprise the same structure and function as described with reference to FIGS. 1-4. The first flow restrictor portion 110 applies an initial smoothing effect to the oscillation of the at least partially pulsatile fluid flow of the fluid before entering the chamber 104B via the chamber inlet. In various embodiments, the pulsatile fluid flow of the fluid may at least partially contact the compliant component 106 of the smoothing device 100A. The pulsatile fluid flow may cause the compliant component 106 to flex from a first position 108A (e.g., initial position) to a second position 108B (e.g., final position). In the embodiment of FIG. 5, the flexing of the compliant component 106 increases the volume of the chamber 104B while reducing the energy of the flow pulse(s).

FIG. 6 illustrates a third volume flow rate smoothing device 100C, which represents a variation of the first embodiment of the volume flow rate smoothing device 100A of FIGS. 1 and 4. In particular, in the depicted embodiment, the compliant component 106 is attached within the bulbous expansion body 105A at or proximate the opening 105C to allow the compliant component to expand into the volume of the bulbous expansion body 105A more evenly. The embodiment of FIG. 6 is otherwise the same as the embodiment of FIG. 4 and interchangeable therewith.

In the embodiment of FIG. 4, the flexing of the compliant component 106 simultaneously reduces the air volume of the second chamber 104A and increases the volume of the chamber 104B. The reduction of the volume of the sealed air in the second chamber 104A and/or the flexible membrane material of the compliant component 106 are configured to absorb and smooth, at least partially, the oscillations and/or pulses of the pulsatile fluid flow. Further, the reduction of the volume of the sealed air chamber portion may cause the pressure within the second chamber 104A to increase. For example, the pressure in the second chamber 104A may be greater in an instance in which the compliant component 106 is in the second position 108B than in an instance in which the compliant component 106 is in the first position 108A.

Turning back to FIG. 5, the depicted second flow restrictor portion 120 may comprise the same structure and function as described with the second flow restrictor portion 120 of FIGS. 1-4. The second flow restrictor portion 120 may further reduce the oscillation and/or pulses of the pulsatile fluid flow of the fluid flow exiting the chamber 104B, such that the fluid comprises a smoother flow, a more constant velocity, and/or a more constant pressure, including but not limited to completely smooth flow. The fluid exits the second flow restrictor portion 120 through the second flow tube 124 towards the flow sensor (shown in FIG. 1).

With reference back to FIG. 1, a flow sensor 130 may be used with the assembly 10 to take measurements (e.g., velocity, pressure, volume flow rate, etc.) of the fluid exiting the smoothing device 100A according to known methods, and the operation of the flow sensor 130 is improved by the more steady flow into the sensor following flow of the pulsatile fluid into the smoothing device 100A and the subsequent reduction of the pulsatile nature of the flow. The fluid flow may be in direct contact with the sensor 130 or the sensor may indirectly measure the flow (e.g., via imaging a transparent tube, such as for nephelometry). The fluid flow after exiting the second flow restrictor portion 120 of any of the foregoing embodiments may be smoother that the flow leaving the pump 200, which may increase the accuracy and precision of the measurements taken by the flow sensor. In some embodiments, the flow sensor 130 may be integrated at least partially to the housing of the volume flow rate smoothing device, wherein the flow sensor can be attached directly to the volume flow rate smoothing device or molded/formed as a single part.

In embodiments using a fluid compliant component 106 (e.g., the depicted embodiments of FIGS. 1-5), the fluid compliant component 106 may use an elastic resilient force to resist pressure from the fluid flow, including flow pulses with greater than average pressure, and the force of the compliant component 106 may be generated as the compliant component flexes back towards a neutral (e.g., unstretched) position. In some embodiments, the first position 108A may be spaced from the neutral position (e.g., $Q_{min}$ while fluid is flowing is greater than $Q_{zero}$ with no flow from the pump). In some embodiments, the fluid compliant component 106 may be a bladder within and either attached or unattached to the volume flow rate smoothing device (e.g., a contained compartment of gas entirely within the fluid compliant component within the volume flow rate smoothing gas).

Many modifications and other embodiments of the present disclosure set forth herein will come to mind to one skilled in the art to which this disclosure pertains having the benefit of the teachings presented in the foregoing description and the associated drawings. Therefore, it is to be understood that the present disclosure is not to be limited to specific embodiments disclosed and that modifications and other embodiments are intended to be included within the scope of the appended claims. Moreover, although the foregoing description and the associated drawings describe example embodiments in the context of certain example combination of elements and/or functions, it should be appreciated, in light of the present disclosure, that different combinations of elements and/or functions than those explicitly described above are also contemplated as can be set forth in some of the appended claims. Although specific terms are employed herein, they are used in a generic and descriptive sense only and not for purpose of limitation.

The invention claimed is:

1. A volume flow rate smoothing device comprising:
 a body portion defining a chamber therein, wherein the body portion includes a bulbous expansion body and a flow body connected to the bulbous expansion body, and wherein the chamber is defined by the flow body and the bulbous expansion body;
 a first flow restrictor portion and a second flow restrictor portion each disposed in fluid communication with the body portion,
 wherein the volume flow rate smoothing device is configured to fluidically communicate with a pump via a first end of the volume flow rate smoothing device to receive a fluid flow from the pump along a fluid pathway extending through the first flow restrictor portion, the body portion, and the second flow restrictor portion, wherein the first flow restrictor portion is disposed upstream of the body portion, and
wherein the second flow restrictor portion is disposed downstream of the body portion.

2. The volume flow rate smoothing device of claim 1, wherein the first flow restrictor portion and the second flow restrictor portion comprise a same minimum hydraulic diameter.

3. The volume flow rate smoothing device of claim 1, the volume flow rate smoothing device further comprises a compliant component located within the body portion.

4. The volume flow rate smoothing device of claim 3, wherein the compliant component comprises a flexible membrane configured to contact at least partially pulsatile fluid flow within the body portion.

5. The volume flow rate smoothing device of claim 4, wherein the flexible membrane is configured to separate the at least partially pulsatile fluid flow from air on an opposite side of the flexible membrane.

6. The volume flow rate smoothing device of claim 5, wherein the body portion defines a sealed air chamber comprising the air.

7. The volume flow rate smoothing device of claim 5, wherein the body portion is configured to permit external air to contact the flexible membrane.

8. The volume flow rate smoothing device of claim 1, wherein the first flow restrictor portion defines a first hydraulic diameter, and wherein the first hydraulic diameter is configured to be less than a hydraulic diameter of a tube configured to couple to the volume flow rate smoothing device at the first end of the volume flow rate smoothing device.

9. The volume flow rate smoothing device of claim 8, wherein the second flow restrictor portion defines a second hydraulic diameter, and wherein the first hydraulic diameter is configured to be less than the hydraulic diameter of the tube.

10. A volume flow rate smoothing assembly comprising:
a volume flow rate smoothing device comprising:
a body portion defining a chamber therein, wherein the body portion includes a bulbous expansion body and a flow body connected to the bulbous expansion body, and wherein the chamber is defined by the flow body and the bulbous expansion body;
a first flow restrictor portion and a second flow restrictor portion each disposed in fluid communication with the body portion,
wherein:
the volume flow rate smoothing device is configured to fluidically communicate with a pump via a first end of the volume flow rate smoothing device to receive a fluid flow from the pump along a fluid pathway extending through the first flow restrictor portion, the body portion, and the second flow restrictor portion,
the first flow restrictor portion is disposed upstream of the body portion, and
the second flow restrictor portion is disposed downstream of the body portion;
a first flow tube configured to operably connect to the first end of the volume flow rate smoothing device downstream of the pump; and
a second flow tube configured to operably connect to a second end of the volume flow rate smoothing device downstream of the second flow restrictor portion.

11. The volume flow rate smoothing assembly of claim 10, further comprising at least one flow sensor, wherein the at least one flow sensor is disposed downstream from the chamber along the fluid pathway, the at least one flow sensor being configured to measure one or more properties of the fluid flow exiting the volume flow rate smoothing device.

12. The volume flow rate smoothing assembly of claim 10, wherein the first flow restrictor portion and the second flow restrictor portion comprises a same minimum hydraulic diameter.

13. The volume flow rate smoothing assembly of claim 10, the volume flow rate smoothing device further comprises a compliant component located within the body portion.

14. The volume flow rate smoothing assembly of claim 13, wherein the compliant component comprises a flexible membrane configured to contact at least partially pulsatile fluid flow within the body portion.

15. The volume flow rate smoothing assembly of claim 14, wherein the flexible membrane is configured to separate the at least partially pulsatile fluid flow from air on an opposite side of the flexible membrane.

16. The volume flow rate smoothing assembly of claim 15, wherein the body portion defines a sealed air chamber comprising the air.

17. The volume flow rate smoothing assembly of claim 15, wherein the body portion is open, such that the body portion is configured to permit external air to contact the flexible membrane.

18. The volume flow rate smoothing assembly of claim 10, further comprising a sensor disposed after the second flow restrictor portion, wherein the sensor is configured to receive fluid after the fluid exits the second flow restrictor portion.

19. A fluid dispensing assembly comprising the volume flow rate smoothing assembly of claim 10 and a pump, wherein the fluid flow from the pump is at least partially pulsatile.

* * * * *